(12) United States Patent
Hwang et al.

(10) Patent No.: US 6,558,930 B2
(45) Date of Patent: May 6, 2003

(54) PHYSIOLOGICALLY ACTIVE MATERIALS FROM CEREALS AND PROCESS FOR PREPARATION THEREOF

(75) Inventors: Jaekwan Hwang, #109-604, Dalbitmaeul, #858, Hwajung-dong, Duckyang-gu, 412-735 Goyang-city, Gyunggi-do (KR); Bosun Park, Seoul (KR); Jungmi Yun, Seoul (KR)

(73) Assignee: Jaekwan Hwang (KR)

( * ) Notice: Subject to any disclaimer, the term of this patent is extended or adjusted under 35 U.S.C. 154(b) by 0 days.

(21) Appl. No.: 09/877,882

(22) Filed: Jun. 8, 2001

(65) Prior Publication Data

US 2002/0037331 A1 Mar. 28, 2002

(30) Foreign Application Priority Data

| Mar. 14, 2000 | (KR) | 2000-12911 |
| May 25, 2000 | (KR) | 2000-28471 |
| Jun. 8, 2000 | (KR) | 2000-31492 |
| Nov. 13, 2000 | (JP) | 2000-67244 |

(51) Int. Cl.⁷ ............................................. C12P 19/04
(52) U.S. Cl. ..................... 435/101; 435/99; 435/72; 435/136; 435/146; 435/267; 435/274
(58) Field of Search ................. 435/101, 136, 435/146, 99, 72, 267, 274

(56) References Cited

U.S. PATENT DOCUMENTS 4,500,558 A    2/1985   Fulger et al. ............... 426/622

FOREIGN PATENT DOCUMENTS

GB           2301103 A    *  11/1996
WO           WO 99/11672  *  3/1999

OTHER PUBLICATIONS

Park et al, J. Ferment. Technol. 65(4):469–473, 1987.*
Rouau et al, J. Cereal Sci. 28:63–70, 1998.*
Mary Ellen Camire et al., "Thermal processing effects on dietary fiber composition and hydration capacity in corn meal, oat meal and potato peels" (1991), Cereal Chem. 68(6): 645–647.
S. Aoe et al., "Extraction of soluble dietary fibers from defatted rice bran" (1993), Cereal Chem. 70(4): 423–425.
Takashi Hayakawa et al., "Influence of extrusion on the physiological effects of brans in rats" (1990), Agric. Biol. Chem. 54(5): 1285–1287.
Ann–Sofie Sandberg et al., "Extrusion cooking of a high–fibre cereal product" (1986), British J. Nutr. 55: 245–254.
Andrea Caprez et al., "Influence of different types of thermal treatment on the chemical composition and physical properties of wheat bran" (1986), J. Cereal Science 4:233–239.

* cited by examiner

*Primary Examiner*—Francisco Prats
(74) *Attorney, Agent, or Firm*—Mathews, Collins, Shepherd & McKay, P.A.

(57) ABSTRACT

The present invention relates to physiologically active materials separated from the cereals and manufacturing method thereof. Physiologically active materials such as ferulic acid and arabinoxylan present in cereal brans were separated by the extrusion process and the subsequent treatment with plant cell wall hydrolyzing enzymes. This combined process of extrusion and enzyme treatments for cereal brans, compared to the individual treatment, significantly increased the separation efficiency of physiologically active materials in cereal brans, ferulic acid and arabinoxylan, which inherently exist as insoluble materials in the cell wall of cereal bran.

6 Claims, 9 Drawing Sheets

PHYSIOLOGICALLY ACTIVE MATERIALS FROM CEREALS AND PROCESS FOR PREPARATION THEREOF

Convention priority for this application is claimed to Korean Patent Application No. 2000-12911 filed Mar. 14, 2000; Korean Patent Application No. 2000-28471 filed May 25, 2000; Korean Patent Application No. 2000-31492 filed Jun. 8, 2000; and Korean Patent Application No. 2000-67244 filed Nov. 13, 2000.

TECHNICAL FIELD

The present invention relates to physiologically active materials separated from cereals and a process for preparation thereof More particularly, the present invention relates to ferulic acid and arabinoxylan, both being of physiological activity, separated from cereal bran and a process for separation thereof, which is a combined process of extrusion and the subsequent treatment with cell wall hydrolyzing enzymes for cereal bran.

BACKGROUND ART

Cereal bran is a byproduct generated in the polishing process. The cereal bran contains a pericarp, a seed coat, an aleurone and the like, exclusive of the hull from the outer layer of cereals and occasionally contains a part of germ and endosperm as a result of the polishing process (Kulp, K. et al., Handbook of Cereal Science and Technology, Marcel Dekker, Inc., Switzerland, 2000).

The cell wall of cereal bran consists of macromolecules such as cellulose, hemicelluloses, lignin, glycoprotein, and the like. These molecules do not exist in free form, but mostly bind strongly to each other via covalent bonds, hydrogen bonds and ionic bonds, existing in insoluble form (Dey, P. M. and Brinson, K. Adv. Carbohydr. Chem. Biochem., 42: 265–382, 1986).

Aside from the above macromolecules, cereal bran contains vitamin and mineral, etc. in the cell wall. Particularly, having been lately characterized as functional active materials, phenolic compounds such as caffeic acid, sinapic acid, ferulic acid and coumaric acid are disclosed (Clifford, M. N. et al., J. Sci. Food. Agric., 79:373–378, 1999).

One of the most abundant phenolic compounds in cereal bran is the ferulic acid represented by the following formula I. It has been known until now that the ferulic acid has several physiological activities such as antioxidant, anticancer, anticholesterol, antibiotic, anti-mutation and anti-inflammatory, etc. (Castelluccio, C. et al., Biochem. J., 316:691–694, 1996; Fernandez, M. A. et al., J. Pharm. Phamacol., 50:1183–1186, 1998; Saija, A. et al., Int. J. Pharmacol., 199:39–47, 2000).

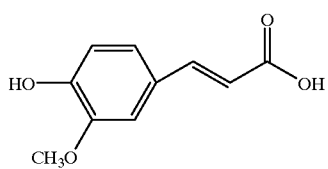

(I)

Ferulic acid does not exist in free form in the cell wall of the cereal bran, but forms an insoluble linkage that is bound to arabinoxylan, one of cell wall components, by ester linkage (Saulnier, L. and Thibault, J. F., J. Sci. Food Agric., 79: 396–402, 1999).

Ferulic acid, though present in cereal bran, has almost no physiological activity, because there are no enzyme systems which can break the ester linkage of ferulic acid and arabinoxylan in the human body. Therefore, very limited bioavailability can be obtained even if cereals are ingested (Saunders, R. M. et al., Cereal Chem., 49:436–442, 1972; Annison, G. et al., World's Poult. Sci. J., 47:232–242, 1991). Arabinoxylan, one of the hemicelluloses constituting the cell wall of cereal bran, is a sort of complex carbohydrate. It has recently been found that arabinoxylan has several physiological activities, such as immunomodulating effect, anti-diabetes, increasing resistance to infection, therapeutic aid versus malignant tumors, water-soluble dietary fiber and the like, and thus has attracted particular attention as a new functional food material (Ghoneum, M., Int. J. Immunother., 104(2): 89–99, 1998; Miyazaki, H. et al., Int. J. Immunophamacol., 16(2): 163–170, 1994; Menon, P. V. et al., J. Nutr., 106(4): 555–562, 1976).

Like ferulic acid, arabinoxylan does not exist in free form in the cell wall of cereal bran, but is present as an insoluble form bound with other cell wall components (Hatfield, R. D. et al., J. Sci. Food Agric., 79: 404–407, 1999). The absence of enzyme systems which can dissolve such insoluble materials in the human body makes the bioavailability of arabinoxylan very low.

Generally, food processing is carried out by steaming, roasting, drying, grinding and the like. Because these cause only physical changes of food, it is very difficult to separate the ferulic acid and arabinoxylan, which exist as insoluble materials in cereal bran, from the other cell wall components.

In addition, the rigid structure of cereal cell walls rarely allows enzymes to infiltrate thereinto owing to its being highly dense, which makes it very difficult to separate insoluble materials in cereal bran by individual enzyme treatment processes.

Because the extrusion process accompanies not only high temperature and pressure, but also a strong shearing force, a rigid structure of plant cell walls is efficiently disintegrated by the extrusion process (Hwang et al., J. Korean Soc. Food Nutr., 23(2):358–370, 1994).

Therefore if cereal bran is treated with individual enzymes, it is difficult for the enzymes to infiltrate into the cell wall structure. But if enzyme treatment follows an extrusion process, it is possible to separate physiologically active materials, since enzymes can readily infiltrate into the cell wall structure, which is already disintegrated by extrusion.

DISCLOSURE OF THE INVENTION

Bearing the above-mentioned backgrounds in mind, the present inventors have accomplished the separation of ferulic acid and arabinoxylan by a combined process, first comprising extrusion in order to physically break down the rigid structure of cereal bran derived from cereals such as rice, wheat, rye, corn, barley, oats and the like, and secondly the subsequent treatment with cell wall hydrolyzing enzymes to hydrolyze insoluble linkages.

Accordingly, it is an object of the present invention to provide physiologically active materials such as ferulic acid and arabinoxylan, which are separated from cereals.

It is another object of the present invention to provide a method of separating physiologically active materials from the above-mentioned cereal.

To accomplish the objects of the present invention, first, cereal bran derived from cereals such as rice, wheat, rye, corn, barley, oats and the like is injected into a twin screw extruder for extrusion, followed by hydrolyzing polymers of the bran with cellulase or hemicellulase, such as arabinase, xylanase, mannase, glucanase and the like, to separate physiologically active materials such as ferulic acid and arabinoxylan.

For the preparation of physiologically active materials from cereal bran, first, cereal bran is physically break down by extrusion from a twin screw extruder. The extrudate is dispersed in water and its cell wall material is decomposed by treatment with hydrolyzing enzymes. Subsequently, the hydrolysate is extracted with ethyl acetate, followed by concentration in vacuo to give ferulic acid. Seperately, the hydrolysate is centrifiltered and the filtrate is added with an α-amylase, such as TERMAMYL 120L (Novozymes A/S, Denmark), for hydrolyzing starch. After ultrafiltration, the residue is dried to dryness to give water-soluble polysaccharides, including arabinoxylan.

BEST MODES FOR CARRYING OUT THE INVENTION

The application of the preferred embodiments of the present invention is best understood with reference to the accompanying drawings.

Figure 1:
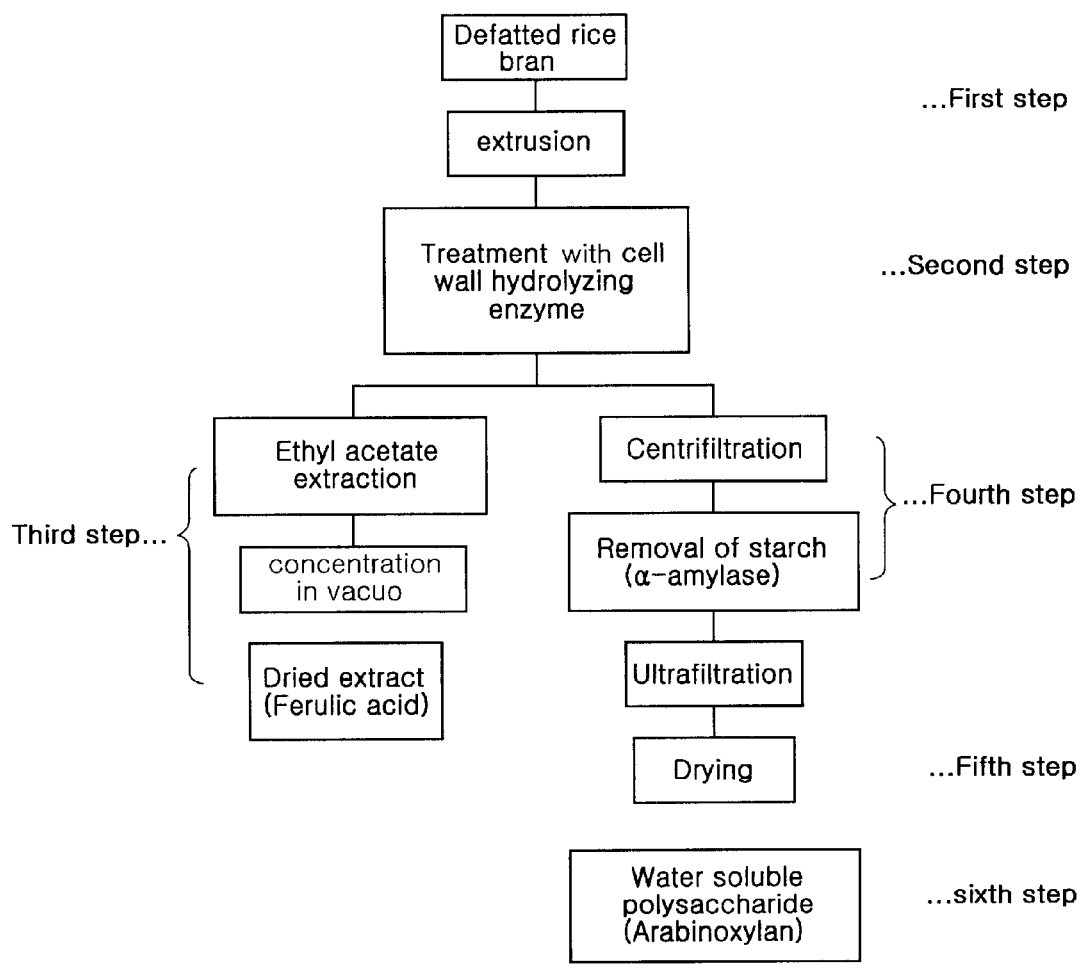
FIG. 1 is a flow diagram briefly showing the preferred embodiment of the method to separate ferulic acid and arabinoxylan from defatted rice bran by the combined process of extrusion and subsequent enzyme treatment.

Referring FIG. 1, there is shown a process of preparing physiologically active materials in accordance with the present invention. The cereal bran useful in the present invention is the bran layer generated in the polishing process of cereals such as rice, wheat, rye, corn, barley, oats, etc.

As seen in the process diagram of FIG. 1, the cereal bran is first extruded. In this regard, a useful extruder is a co-rotating intermeshed type twin-screw extruder (Buhler Brothers Co. DNDL-40, Switzerland) with an L/D ratio of 20:1. Preferably, the extrusion is conducted under conditions, including a screw rotation rate of 200~400 rpm, a feed rate of 20~50 kg/hr, a moisture content of 15~40% and a temperature of 100~200° C. Examples of the extruder to break down the solid cell wall structure of cereal bran include a single screw extruder and a twin screw extruder with preference for the twin screw extruder.

In the next step, the extrudates are subjected to cell wall decomposition in the presence of a cell wall hydrolyzing enzyme system. In accordance with the present invention, the cell wall hydrolyzing enzyme system is comprised of at least two enzymes selected from the group consisting of cellulase, arabinase, xylanase, mannase and glucanase, and they may be used separately or together.

The cell wall hydrolyzing enzymes useful in the present invention may be commercially available, for example, exemplified by CELLUCLAST (Novozymes A/S, Denmark), ECONASE HC400 (Econase Co., Finland), CEREMIX (Novozymes A/S, Denmark). These enzymes are used in equal weight proportions. In this invention the above-exemplified commercial enzymes without purification are preferred because they contain various enzymes such as cellulase, β-glucanase, arabinase, xylanase, mannase and the like. That is, these complex enzymes can effectively hydrolyze the cell walls of cereal composed of complex carbohydrates.

In accordance with the present invention, the hydrolyzing enzymes are preferably used in a weight ratio of 1:0.001~1:0.1 to the cereal bran extrudate used. The enzymatic hydrolysis is preferably conducted at 30 to 60° C. for 0.5 to 12 hours.

The present invention will be more apparent by the following embodiments and experiments thereof, but which do not limit the scope of the present invention.

EXAMPLE 1

Separation of Ferulic Acid From Rice Bran by the Combined Process of Extrusion and Subsequent Enzyme Treatment Milled, defatted rice bran was injected into a corotating intermeshed type twin-screw extruder (Buhler Brothers Co. DNDL-40, Switzerland). The extrusion process was performed under the conditions of screw rotation rate of 300 rpm, feed rate of 30 kg/hr, moisture content of 30% and temperature of 150° C. 1 g of the rice bran extrudate thus obtained was dispersed in 20 L of water. Then, 10 mL of enzyme, comprising CELLUCLAST (Novozymes A/S, Denmark), ECONASE HC 400 (Econase Co., Finland) and CEREMIX (Novozymes A/S, Denmark) in 1:1:1 weight ratio, was added to the dispersed solution, followed by conducting hydrolyzing reactions for 2 hours at a temperature of 60° C. with stirring. From the hydrolysate, materials of interest were extracted with 20 L of ethyl acetate. Then, the extract was divided to smaller volumes which were then concentrated in vacuo to leave a residue containing felulic acid.

Experiment 1

Production Yield of Ferulic Acid 0.1 g of the extract prepared in Example 1 was dissolved in 10 L of a mixture of methanol and water in the volume proportion of 1:1, followed by measuring the feluric acid level therein with the aid of a capillary electrophoresis apparatus (Beckman Inc., USA) using a fused silica capillary column with a buffer solution of 0.1 M borate.

The sample was injected for 3 seconds under pressure at 25° C. in an electric field of 25 kV. Quantification of the ferulic acid was achieved using a pulsed diode array (PDA) detecter.

In order to measure the total amount of the ferulic acid, 20 L of 1N NaOH was added to 1 Kg of rice bran which was then subjected to enzymatic hydrolysis for 1 hour at 25° C. and dried to obtain ferulic acid. In the manner same as in Example 1, the ferulic acid was extracted and quantified using capillary electrophoresis.

Figure 2:
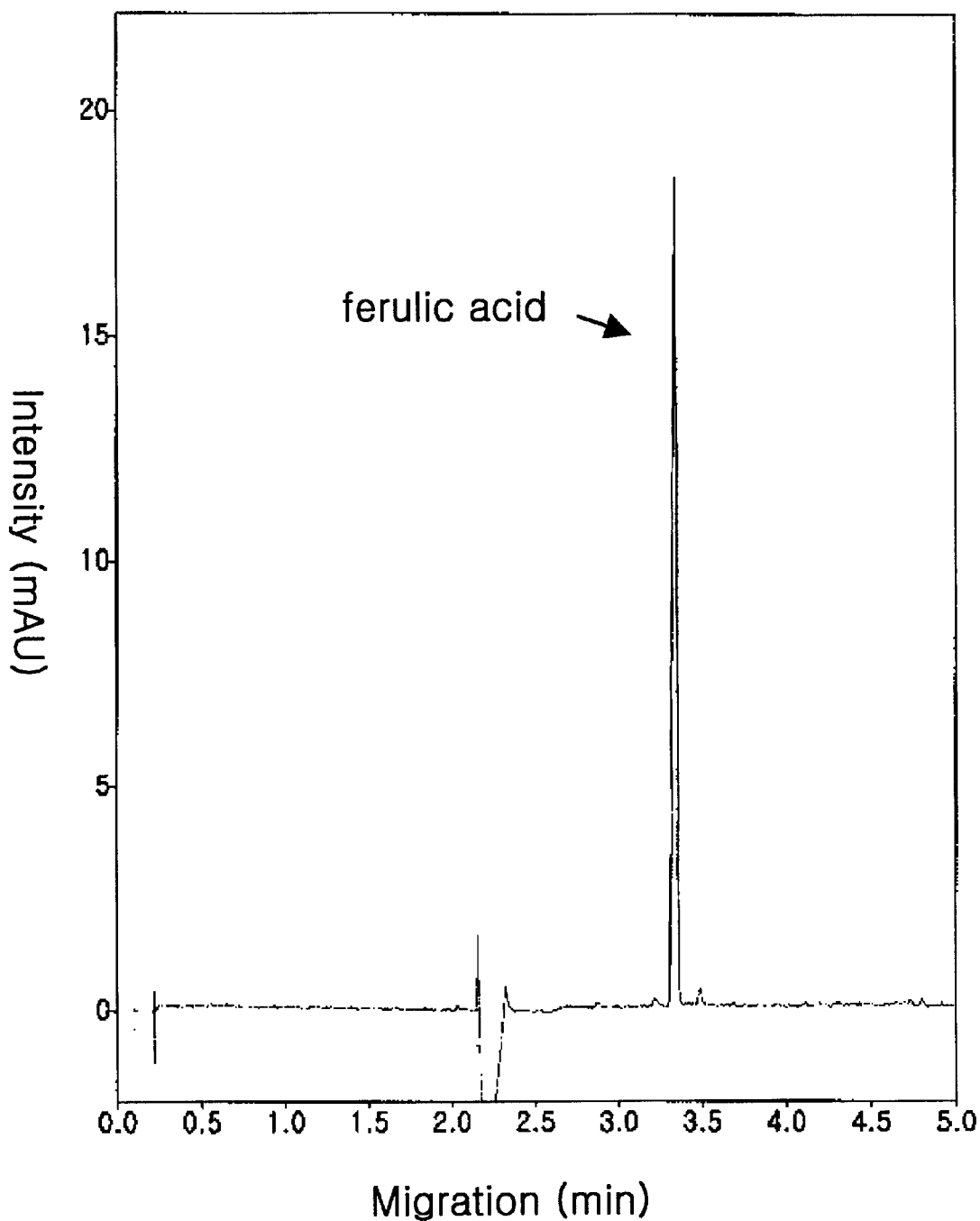
FIG. 2 is a capillary electropherogram showing the total amount of ferulic acid separated from defatted rice bran by NaOH treatment.

FIG. 2 shows total ferulic acid separated from defatted rice bran by NaOH treatment under the above capillary electrophoresis conditions.

Figure 3:
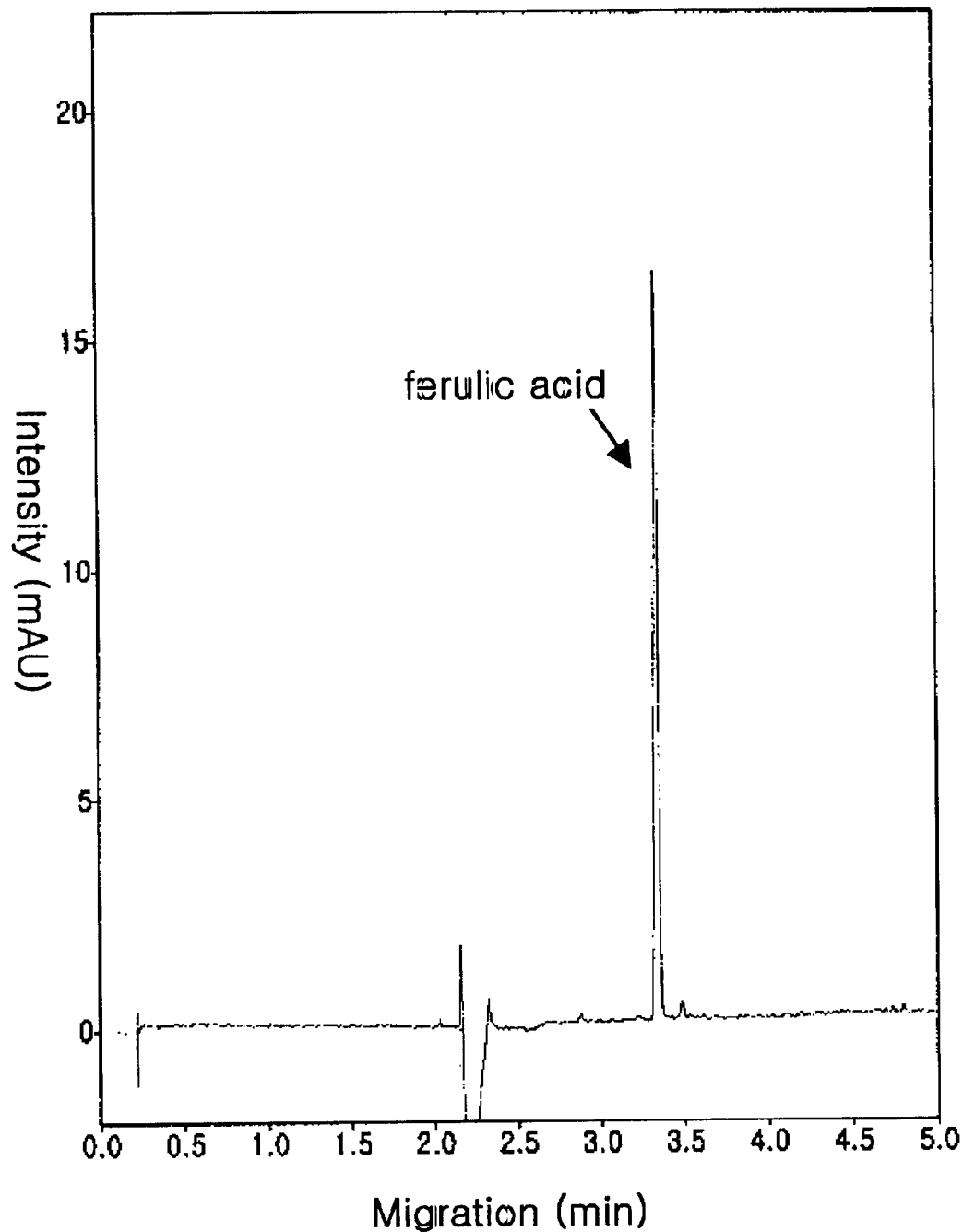
FIG. 3 is a capillary electropherogram showing the total amount of ferulic acid separated from defatted rice bran by the combined process of the extrusion and the subsequent enzyme treatment.

FIG. 3 shows ferulic acid separated from defatted rice bran by the combined process of extrusion and subsequent enzyme treatment under the above capillary electrophoresis conditions.

Figure 4:
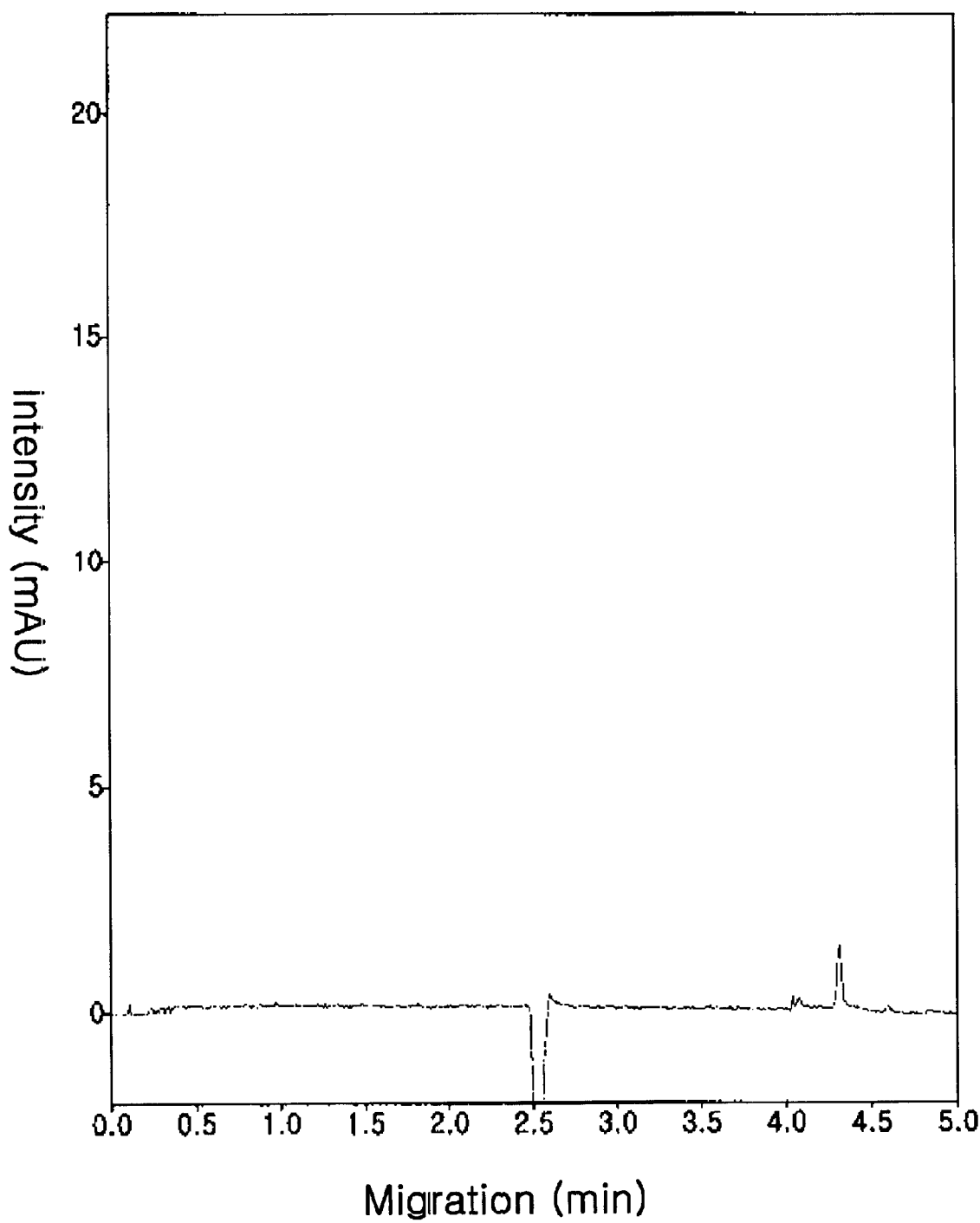
FIG. 4 is a capillary electropherogram showing the total amount of ferulic acid separated from defatted rice bran by the extrusion process alone.

FIG. 4 shows ferulic acid separated from defatted rice bran by the extrusion process alone under the above capillary electrophoresis conditions.

Figure 5:
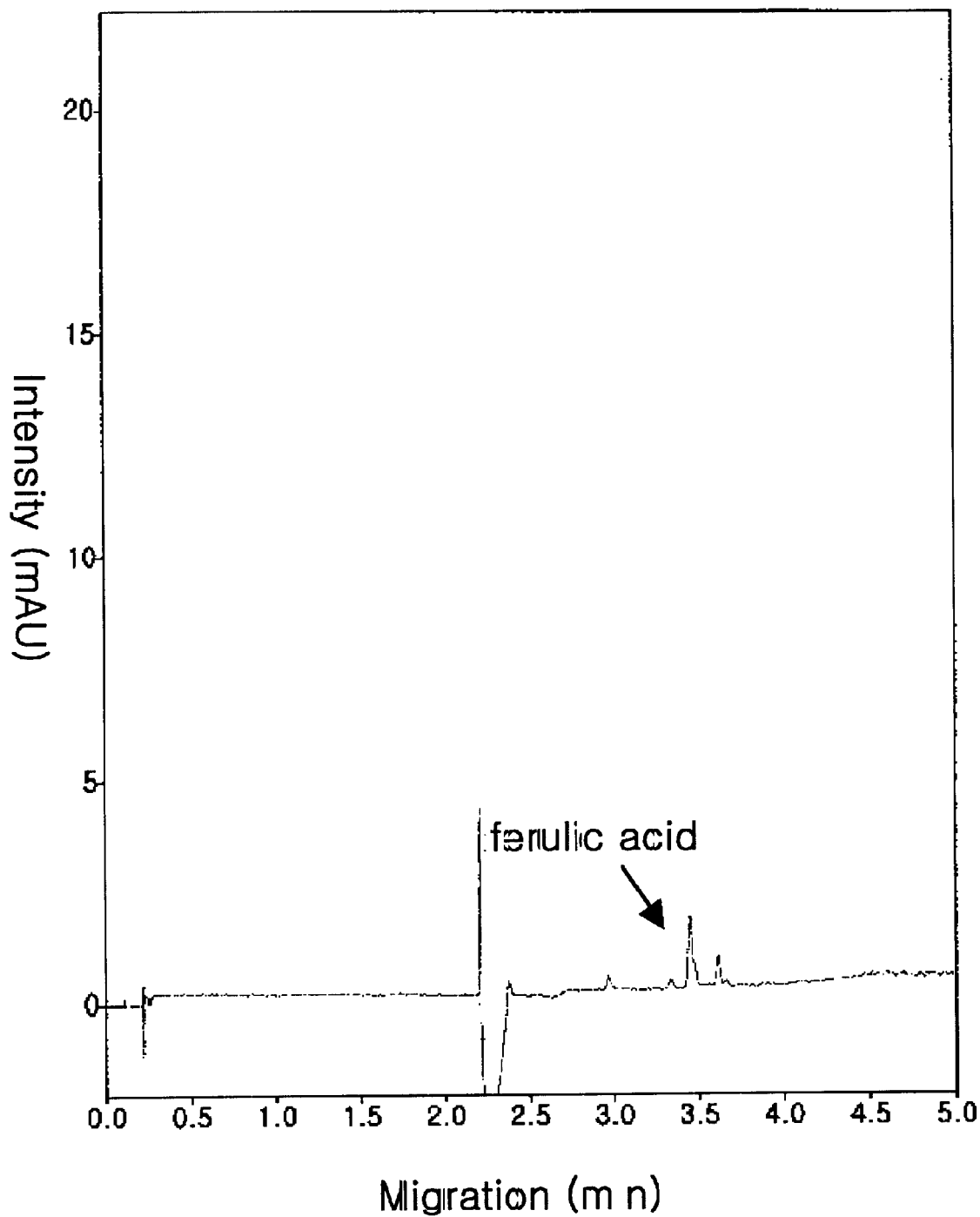
FIG. 5 is a capillary electropherogram showing the total amount of ferulic acid separated from defatted rice bran by the enzyme treatment alone.

FIG. 5 shows ferulic acid separated from defatted rice bran by the enzyme treatment alone, under the above capillary electrophoresis conditions.

The following table 1 shows an amount of the ferulic acid separated from rice bran and a relative yield on the basis of an amount of ferulic acid separated by NaOH treatment.

TABLE 1

Content of ferulic acid separated from rice bran and relative yield

| Sample | Content of ferulic acid in sample (%, w/w) | Relative yield of ferulic acid (%) |
|---|---|---|
| NaOH Treatment | 0.27 | 100 |
| Extrusion & subsequent enzyme treatment | 0.22 | 81.5 |
| Extrusion alone | 0 | 0 |
| Enzyme Treatment alone | 0.02 | 7.4 |

As seen in Table 1, ferulic acid, which was associated with other cell wall components, existing in insoluble form, was separated in free form at high yield by the combined process of extrusion and subsequent enzyme treatment. As much as about 81.5% of the total ferulic acid was isolated in free form from insoluble form. As for the individual process used alone, they were very poor in separation yield of ferulic acid.

EXAMPLE 2

Separation of Arabinoxylan From Rice Bran by the Combined Process of Extrusion and Subsequent Enzyme Treatment Milled, defatted rice bran was injected into a corotating intermeshed type twin-screw extruder (Buhler Brothers Co. DNDL-40, Switzerland). The extrusion process was performed under the conditions of screw rotation rate of 300 rpm, feed rate of 30 kg/hr, moisture content of 30% and temperature of 150° C. 1 kg of the rice bran extrudate thus obtained was dispersed in 20 L of water. Then, 10 mL of enzyme, comprising CELLUCLAST (Novozymes A/S, Denmark), ECONASE HC 400 (Econase Co., Finland) and CEREMIX (Novozymes A/S, Denmark) in equal weight, was added to the dispersed solution, followed by conducting hydrolyzing reactions for 2 hours at a temperature of 60° C. with stirring. After filtration through a centrifugal filter, the filtrate was added with 10 mL of TERMAMYL 120L (Novozymes A/S, Denmark) and its starch was hydrolyzed at 90° C. for 1 hour. The resulting hydrolysate was filtered using an ultrafiltrator having a filter membrane with molecular weight cutoff 5,000. The ultrafitrate was concentrated to dryness to give water-soluble polysaccharides including arabinoxylan.

Experiment 2

Content of Arabinoxylan in the Water Soluble Polysaccharides 1.2 mL of 2N sulfuric acid was added to 1 mg of the water soluble polysaccharides prepared in Example 2 and then the resulting solution was heated for 3 hours at 100° C. to produce neutral sugars. The content of arabinoxylan was determined as the sum of the contents of arabinose and xylose. Quantification of the neutral sugars resorted to Bio-LC (Dionex DX-500, USA) using Carbopac™ PA1 with isocratic eluent of 22.6 mM NaOH solution and a regeneration buffer of 200 mM NaOH solution. The injection volume was 50 µL while the flow rate of isocratic eluent was 0.3 mL/min with detection of the eluate by means of an electro-chemical detector (ECO).

For comparison, water soluble polysaccharides were prepared from rice bran by NaOH treatment. To this end, first, 1 kg of rice bran was added with 20 L of 1N NaOH, and the pH of the solution was adjusted to 6 with 1N HCl. Then, starch removal and ultrafiltration were conduced in the manner same as Example 2 to give water soluble polysaccharides.

Figure 6:
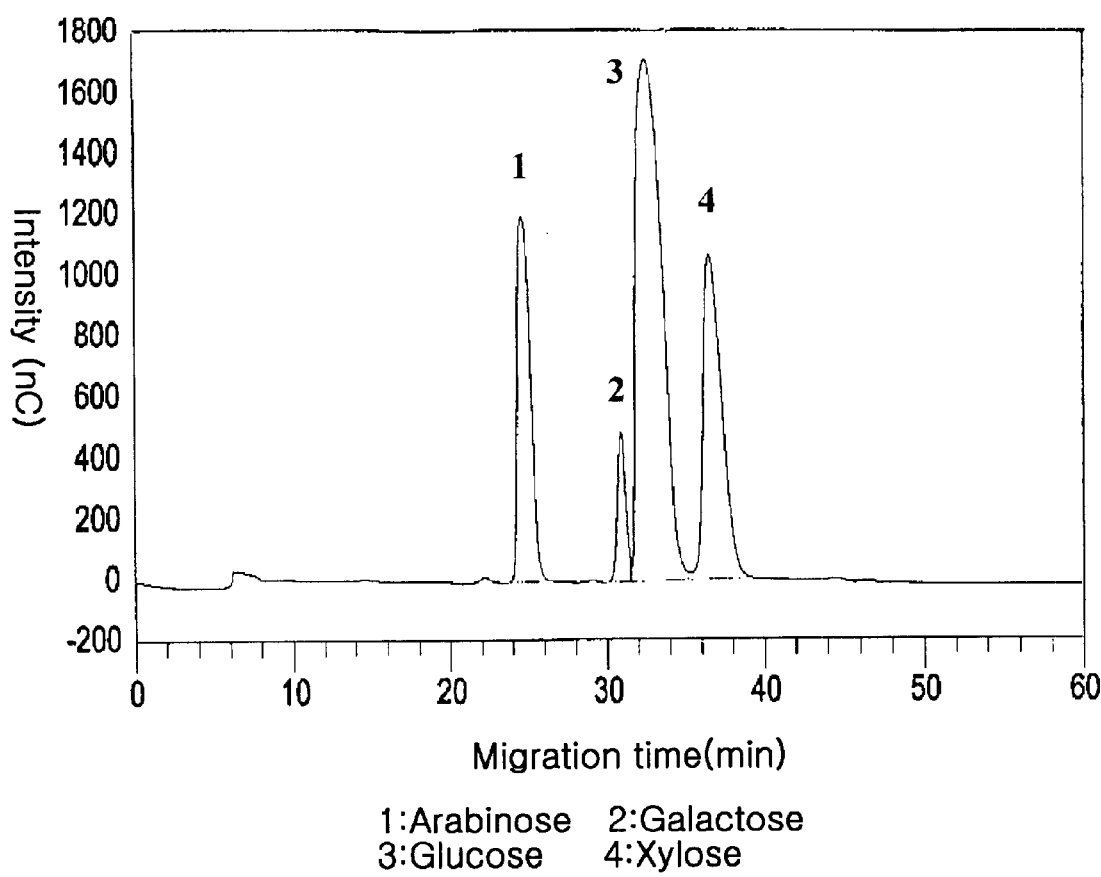
FIG. 6 is a graph showing the proportion of neutral sugars in water soluble polysaccharides separated from defatted rice bran by NaOH treatment.

FIG. 6 is a graph showing the distribution of neutral sugars in the water soluble polysaccharides separated from defatted rice bran by NaOH treatment as measured under the above conditions for Bio-LC.

Figure 7:
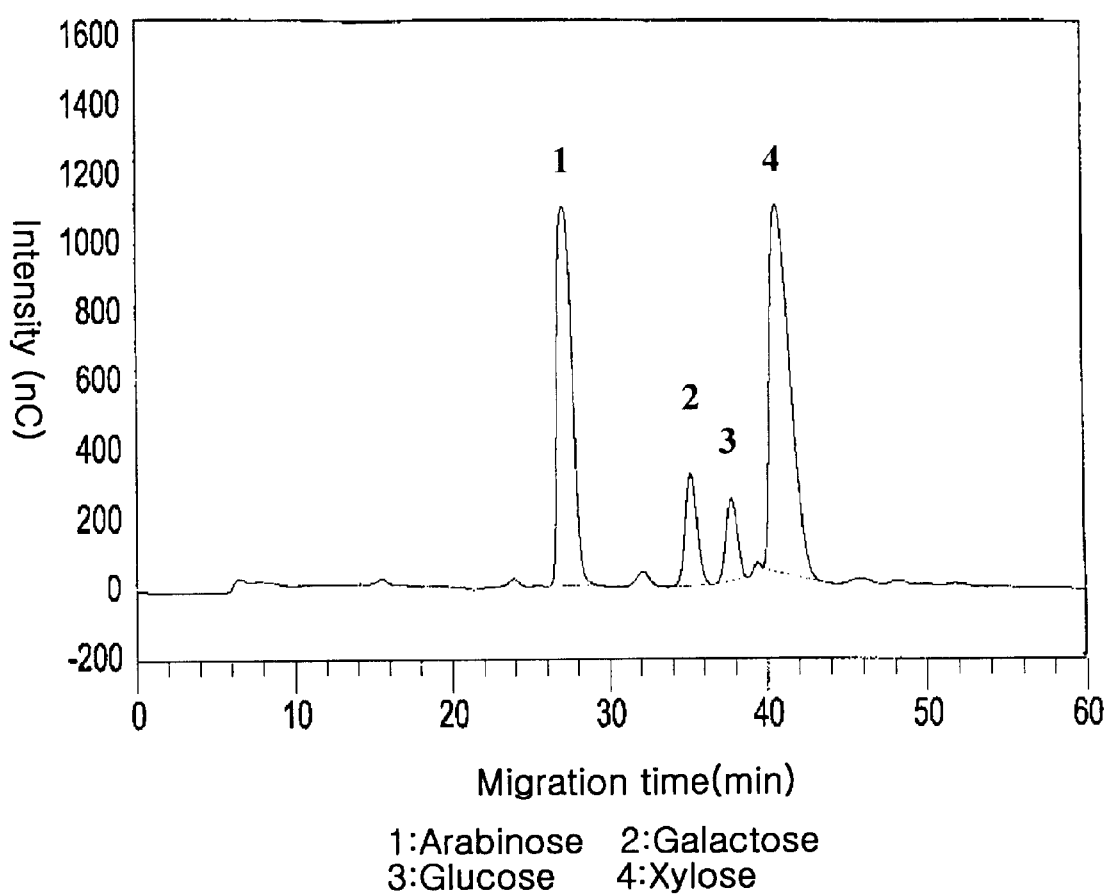
FIG. 7 is a graph showing the proportion of neutral sugars in water soluble polysaccharides separated from defatted rice bran by the combined process of the extrusion and the subsequent enzyme treatment.

FIG. 7 is a graph showing the distribution of neutral sugars in the water soluble polysaccharides separated from defatted rice bran by the combined process of the extrusion and subsequent enzyme treatment as measured under the above conditions for Bio-LC.

The following table 2 shows a yield of water soluble polysaccharides separated from rice bran by each process and the distribution of neutral sugars by each process.

TABLE 2

Yield of water soluble polysaccharides separated from rice bran and the distribution of neutral sugars.

| Sample | Yield (%, w/w) | Amount of neutral sugars (mole %) | | | | |
|---|---|---|---|---|---|---|
| | | arabinose | xylose | galactose | glucose | mannose |
| NaOH Treatment | 15.9 | 21.1 | 31.6 | 4.1 | 43.2 | 0.0 |
| Extrusion & enzyme treatment | 16.2 | 33.6 | 56.9 | 3.3 | 6.2 | 0.0 |
| Extrusion alone | 2.2 | 23.6 | 20.1 | 12.0 | 30.5 | 13.8 |
| Enzyme treatment alone | 1.6 | 28.1 | 30.2 | 11.2 | 20.9 | 9.6 |

As shown in Table 2, the combined process is similar in production yield to NaOH treatment. In contrast, the extrusion or the enzyme treatment, when being adopted alone, showed a very low yield for water soluble polysaccharides.

Particularly when using the combined process, the total amount of arabinose and xylose was measured to amount to 90.5 mole %, which was much higher than the total amount obtained by NaOH treatment, that is, 52.7 mole %. This means that the purity of arabinoxylan produced by the combined process is very high, compared with NaOH treatment.

Therefore, compared with each individual process, the combined process greatly increases the production yield of water soluble polysaccharides and amount of arabinoxylan.

Experiment 3
Molecular Weight of Water Soluble Polysaccharides 0.01 g of the water soluble polysaccharides prepared in Example 2 was dispersed in 10 mL of distilled water, and measured for molecular weight distribution by means of gel permeation chromatography (GPC) (Alliance 2690, Waters, USA) using a column filled with a combination of Ultrahydrogel linear and Ultrahydrogel 500. As an isocratic eluent, 0.1N $NaNO_3$ was used with a flow rate of 1.0 mL/min. The injection volume was 100 µL and the detector was a refractive index detector. The column was maintained at 45° C. and the detector was maintained at 35° C.

For comparison, water soluble polysaccharides were prepared from rice bran by NaOH treatment. To this end, first, 1 kg of rice bran was added with 20 L of 1N NaOH, and the pH of the solution was adjusted to 6 with 1N HCl. Then, starch removal and ultrafiltration were conduced in the manner same as Example 2 to give water soluble polysaccharides.

Figure 8:
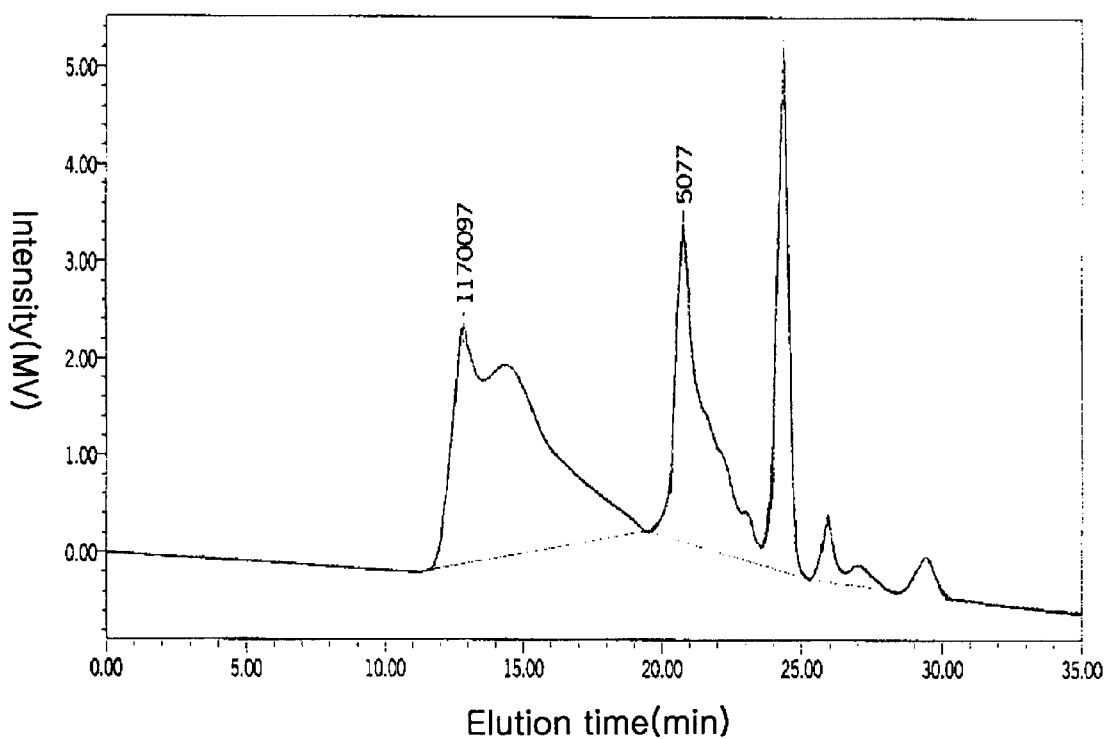
FIG. 8 is a graph showing the molecular weight distribution of water soluble polysaccharides separated from defatted rice bran by NaOH treatment.

FIG. 8 is a graph showing the molecular weight distribution of water soluble polysaccharides separated from defatted rice bran by NaOH treatment as measured under the above conditions for GPC.

Figure 9:
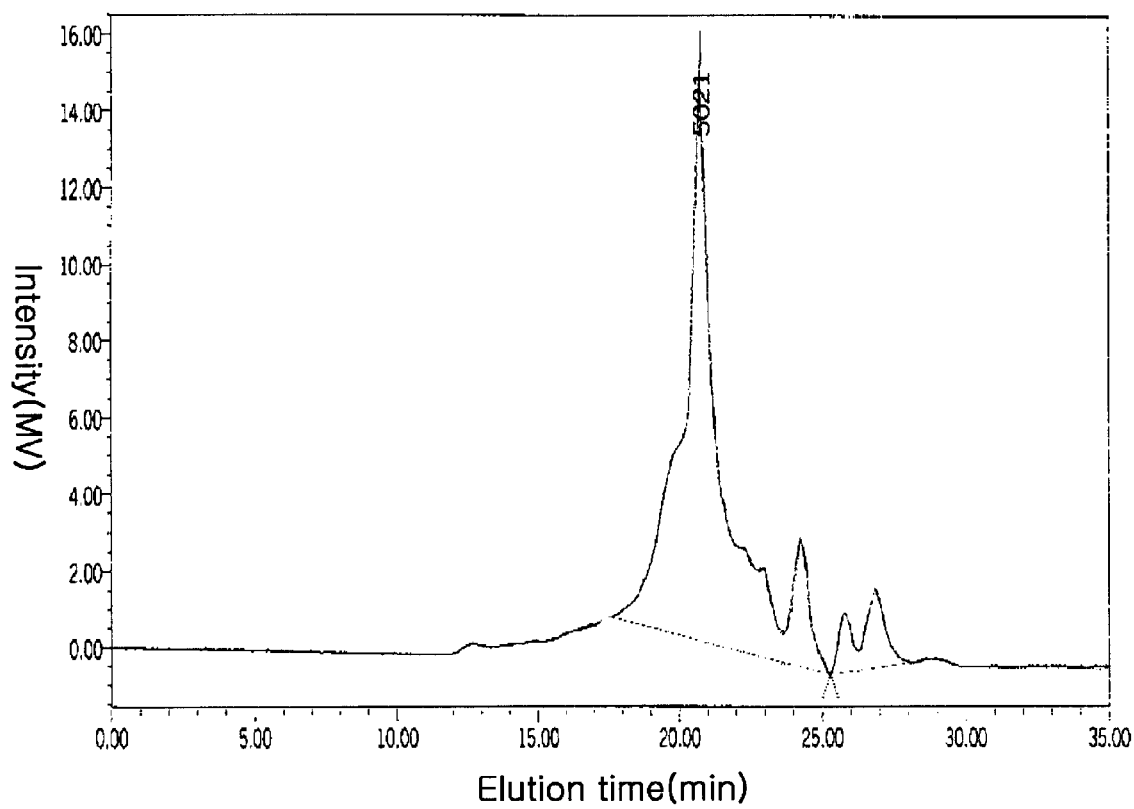
FIG. 9 is a graph showing the molecular weight distribution of water soluble polysaccharides separated from defatted rice bran by the combined process of the extrusion and the subsequent enzyme treatment.

FIG. 9 is a graph showing the molecular weight distribution of water soluble polysaccharides separated from defatted rice bran by the combined process of extrusion and subsequent enzyme treatment as measured under the above conditions for GPC.

As seen in the graphs, the water soluble polysaccharides prepared by alkali treatment have a broad range of molecular weights ranging from about 5,000 to 1,170,000, while the arabinoxylan prepared by the combined process has a mean molecular weight of about 5,000 with a uniform molecular weight distribution.

EXAMPLE 3

Separation of Physiologically Active Materials From Wheat Bran

Physiologically active materials were separated from wheat bran by the combined process of extrusion and subsequent enzyme treatment as in Examples 1 and 2. The separated ferulic acid was found to amount to 84.6% of the total ferulic acid present in wheat bran as measured in the same manner as in Experiment 1. As for the separated arabinoxylan, its amount was measured to be 15.2% of the total weight of the wheat bran, measured in the same manner as in Experiment 2.

EXAMPLE 4

Separation of Physiologically Active Materials From Rye Bran

Physiologically active materials were separated from rye bran by the combined process of extrusion and subsequent enzyme treatment as in Examples 1 and 2. The separated ferulic acid was found to amount to 78.5% of the total ferulic acid present in rye bran as measured in the same manner as in Experiment 1. As for the separated arabinoxylan, its amount was measured to be 13.5% of the total weight of the rye bran, measured in the same manner as in Experiment 2.

EXAMPLE 5

Separation of Physiologically Active Materials From Corn Bran

Physiologically active materials were separated from corn bran by the combined process of extrusion and subsequent enzyme treatment as in Examples 1 and 2. The separated ferulic acid was found to amount to 78.5% of the total ferulic acid present in corn bran as measured in the same manner as in Experiment 1. As for the separated arabinoxylan, its amount was measured to be 13.5% of the total weight of the corn bran, measured in the same manner as in Experiment 2.

EXAMPLE 6

Separation of Physiologically Active Materials From Barley Bran

Physiologically active materials were separated from barley bran by the combined process of extrusion and subsequent enzyme treatment as in Examples 1 and 2. The separated ferulic acid was found to amount to 78.5% of the total ferulic acid present in barley bran as measured in the same manner as in Experiment 1. As for the separated arabinoxylan, its amount was measured to be 11.9% of the total weight of the barley bran, measured in the same manner as in Experiment 2.

EXAMPLE 7

Separation of Physiologically Active Materials From Oat Bran

Physiologically active materials were separated from oat bran by the combined process of extrusion and subsequent enzyme treatment as in Examples 1 and 2. The separated ferulic acid was found to amount to 69.2% of the total ferulic acid present in oat bran as measured in the same manner as in Experiment 1. As for the separated arabinoxylan, its amount was measured to be 15.2% of the total weight of the oat bran, measured in the same manner as in Experiment 2.

Industrial Applicability

Compared to the extrusion process or the enzyme treatment process alone, as described hereinbefore, the combined process of extrusion and subsequent enzyme treatment for cereal bran remarkably increases the separation efficiency of the physiologically active materials, ferulic acid and arabinoxylan, so that the present invention will be very useful in the food processing industry.

What is claimed is:

1. A method for preparing ferulic acid in free form from cereal bran comprising the steps of:

(a) injecting milled defatted cereal bran into a corotating intermeshed twin screw extruder with a feed rate of about 20 to about 50 kg/hr;

(b) maintaining the screw rate at about 200 to about 500 revolutions per minute, the moisture content at about 15 to about 40% and the temperature at about 100 to about 200° C.;

(c) suspending the extrudate in water and adding cell-wall hydrolyzing enzymes in a weight ratio of about 1.0:0.001 to about 1.0:0.1 and maintaining the mixture with stirring at about 30 to about 60 minutes at a temperature of about 30 to about 60° C., (d) extracting the hydrolysate with ethyl acetate, evaporating the ethyl acetate and recovering the ferulic acid.

2. The method as set froth in claim 1 wherein said cereal bran is selected from the group consisting of rice bran, wheat bran, rye bran, corn bran, barley bran and oat bran.

3. The method as set forth in claim 1, wherein said cell wall hydrolyzing enzymes are cellulase and hemicellulase selected from the group consisting of arabinase, xylase, mannose and glucanase.

4. A method for preparing water-soluble arabinoxylan from cereal bran comprising the steps of:
(a) injecting milled defatted cereal bran into corotating intermeshed twin screw extruder with a feed rate of about 20 to about 50 kg/hr;
(b) maintaining the screw rate at about 200 to about 500 revolutions per minute, the moisture content at about 15 to about 40% and the temperature at about 100 to about 200° C.;
(c) suspending the extrudate in water and adding cell-wall hydrolyzing enzymes in a weight ratio of about 1.0:0.001 to about 1.0:0.1 and maintaining the mixture with stirring at about 30 to about 60 minutes at a temperature of about 30 to about 60° C.;
(d) filtering the extrudate through a centrifugal filter and adding starch and α-amylase to said filtrate and maintaining the filtrate at about 90° C. for about one hour;
(e) filtering the hydrolysate using an ultrafiltrator, concentrating the filtrate to dryness, and collecting the water-soluble polysaccharides including arabinoxylan.

5. The method as set forth in claim 4, wherein said cereal bran is selected from the group consisting of rice bran, wheat bran, rye bran, corn bran, barley bran and oat bran.

6. The method as set forth in claim 4, wherein said cell wall hydrolyzing enzymes are cellulase and/or hemicellulase, in which the hemicellulase is selected from the group consisting of arabinase, xylanase, mannose and glucanase.

* * * * *